(12) United States Patent
Aoba et al.

(10) Patent No.: US 9,510,962 B2
(45) Date of Patent: Dec. 6, 2016

(54) STENT DELIVERY SYSTEM

(75) Inventors: Daisuke Aoba, Tokyo (JP); Yutaka Yanuma, Tokyo (JP); Kenji Shibaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1755 days.

(21) Appl. No.: 11/454,821

(22) Filed: Jun. 16, 2006

(65) Prior Publication Data
US 2007/0293929 A1 Dec. 20, 2007

(51) Int. Cl.
*A61F 2/06* (2013.01)
*A61F 2/95* (2013.01)
*A61F 2/04* (2013.01)

(52) U.S. Cl.
CPC ............ *A61F 2/95* (2013.01); *A61F 2002/041* (2013.01); *A61F 2002/9505* (2013.01); *A61F 2002/9511* (2013.01); *A61F 2002/9517* (2013.01); *A61F 2220/0016* (2013.01)

(58) Field of Classification Search
CPC ................. A61F 2/95; A61F 2220/0016; A61F 2002/041; A61F 2002/9511; A61F 2002/9505; A61F 2002/9517
USPC ................................................ 623/1.11, 1.12
See application file for complete search history.

(56) References Cited

U.S. PATENT DOCUMENTS

| | | | |
|---|---|---|---|
| 4,552,554 A * | 11/1985 | Gould et al. | 604/506 |
| 5,147,317 A * | 9/1992 | Shank et al. | 604/164.13 |
| 5,242,452 A | 9/1993 | Inoue | |
| 5,334,185 A | 8/1994 | Giesy et al. | |
| 5,372,600 A * | 12/1994 | Beyar et al. | 623/1.11 |
| 5,405,378 A | 4/1995 | Strecker | |
| 5,653,748 A | 8/1997 | Strecker | |
| 5,921,952 A | 7/1999 | Desmond, III et al. | |
| 6,019,779 A * | 2/2000 | Thorud et al. | 606/198 |
| 6,190,350 B1 * | 2/2001 | Davis et al. | 604/61 |

(Continued)

FOREIGN PATENT DOCUMENTS

| | | |
|---|---|---|
| EP | 1 842 508 A1 | 10/2007 |
| EP | 1 867 305 A2 | 12/2007 |

(Continued)

OTHER PUBLICATIONS

U.S. Office Action mailed Nov. 9, 2010, in related U.S. Appl. No. 12/136,992.

(Continued)

*Primary Examiner* — Richard Louis
(74) *Attorney, Agent, or Firm* — Scully, Scott, Murphy & Presser, P.C.

(57) ABSTRACT

This stent delivery system includes: a guide catheter inserted into the inside of a cylindrical stent, and inserted into the interior of the living body with the stent; a pusher catheter inserted into the interior of the living body with the guide catheter in a state where the guide catheter is inserted into the inside of the push catheter, and which is for pushing the stent along the guide catheter; a stent connecting member for connecting the stent with the pusher catheter; and a stent releasing member for releasing the stent from the pusher catheter by separating the connection between the stent and the pusher catheter depending on the stent connecting member, which is independently operable separately from the guide catheter, and which is inserted into the inside of the pusher catheter.

14 Claims, 16 Drawing Sheets

(56) References Cited

U.S. PATENT DOCUMENTS

| | | |
|---|---|---|
| 6,264,624 B1 | 7/2001 | Desmond, III et al. |
| 6,562,024 B2 | 5/2003 | Alvarez de Toledo et al. |
| 2001/0018574 A1* | 8/2001 | Toledo et al. ............ 604/164.09 |
| 2002/0043313 A1* | 4/2002 | Statnikov ...................... 148/558 |
| 2004/0049256 A1 | 3/2004 | Yee |
| 2005/0027305 A1* | 2/2005 | Shiu et al. .................... 606/108 |
| 2005/0085891 A1* | 4/2005 | Goto et al. ................... 623/1.11 |
| 2005/0085892 A1* | 4/2005 | Goto et al. ................... 623/1.12 |
| 2005/0119722 A1* | 6/2005 | Styrc et al. .................. 623/1.12 |
| 2006/0036307 A1 | 2/2006 | Zarembo et al. |
| 2006/0184224 A1 | 8/2006 | Angel |
| 2006/0195117 A1 | 8/2006 | Rucker et al. |
| 2007/0233223 A1 | 10/2007 | Styrc |
| 2009/0099640 A1 | 4/2009 | Weng |

FOREIGN PATENT DOCUMENTS

| | | |
|---|---|---|
| JP | 11-076419 A | 3/1999 |
| JP | 2000-152985 A | 6/2000 |
| WO | WO 99/08740 | 2/1999 |
| WO | WO 03/092782 A1 | 11/2003 |
| WO | WO 2007/070792 A2 | 6/2007 |
| WO | WO 2007/115483 A1 | 10/2007 |

OTHER PUBLICATIONS

Extended Partial European Search Report dated Sep. 2, 2009.
Japanese Office Action dated Jun. 5, 2012 in Japanese Patent Application No. 2007-157551.

* cited by examiner

STENT DELIVERY SYSTEM

BACKGROUND OF THE INVENTION

Field of the Invention

The present invention relates to a stent delivery system for placing a stent into a hollow region included in the alimentary system, the respiratory system, the urinary system, the reproduction system or the like.

Description of the Related Art

In a case where a stricture or an obstruction arises somewhere in a hollow organ included in the alimentary system, the respiratory system, the urinary system, the reproduction system or the like, in order to recover the real function of the hollow organ, a path is ensured in the hollow organ by placing a stent into the stricture or obstruction. Recently, the operation for placing a stent into a diseased part of the hollow organ which requires treatment is commonly performed using an endoscope and exclusive instruments. For example, in the document of U.S. Pat. No. 5,921,952, a stent delivery system used in the above-mentioned operation is disclosed. In particular, the system includes a guide catheter, a guide wire, a push catheter, and a suture for detachably connecting a stent to a tip of the push catheter. The guide catheter is inserted into the inside of the stent, and inserted into the interior of the living body with the stent. The guide wire guides the guide catheter and the stent to the interior of the living body so as to be inserted into the inside of the guide catheter. The push catheter is inserted into the interior of the living body with the guide catheter in a state where the guide catheter is inserted into the inside of the push catheter, and is used for pushing the stent along the guide catheter. Both ends of the suture are tied to each other, in a state where the suture is laced through a hole formed at a head section of the push catheter. Further, a part of the suture is inserted into the inside of the stent through a hole formed at the stent, and forms a loop. Since a head section of the guide catheter is inserted into the loop, the suture is not separated from the stent. That is, the stent is detachably connected with the tip of the push catheter through the suture.

With the operation, first, the four members are joined as mentioned above, that is, the stent, the guide catheter, the push catheter and the suture are inserted into a channel of an endoscope along the guide wire, then the members are protruded from a tip of a insertion portion of the endoscope. The stent and the head section of the guide catheter are inserted into an affected part of a hollow organ which requires a procedure.

Next, in a state where the guide wire and the push catheter are held in place, the guide catheter is retracted by pulling it from the channel of the insertion portion of the endoscope. At this time, it is not always necessary to retract the entire guide catheter. When the guide catheter is pulled, the head section of the guide catheter is retracted away from the loop of the suture, accordingly the constraint of the stent by the guide catheter is eliminated. Next, similarly to the guide catheter, the guide wire is retracted by pulling the guide wire so as to retract it from the channel of the insertion portion of the endoscope. At this time, also it is not always necessary to retract the entire guide wire. When the guide wire is pulled, the tip of the guide wire is retracted away from the loop of the suture, accordingly the constraint of the stent by the guide catheter is eliminated. As a result, the engagement between the stent and the push catheter through the suture is separated.

Next, when the push catheter is pulled so as to retract it from the channel of the insertion portion of the endoscope, since the engagement between the stent and the push catheter has been separated already, only the stent is placed at the affected part of a hollow organ which requires a procedure.

With the operation as mentioned above, when the stent and the head section of the guide catheter are inserted into the affected part of a hollow organ which requires procedure, if the stent is placed at a position which is deeper than the affected part, the push catheter is pulled slightly before pulling the guide catheter or the guide wire, that is, before separating the engagement between the stent and the push catheter. Therefore, it is possible to replace the stent connected with the tip of the push catheter to the desired position.

SUMMARY OF THE INVENTION

The stent delivery system of the present invention is for placing a cylindrically-shaped stent at the desired position within a living body, the system including: a guide catheter inserted into the inside of the stent, and inserted into the interior of the living body with the stent; a pusher catheter inserted into the interior of the living body with the guide catheter in a state where the guide catheter is inserted into the inside of the push catheter, and which is for pushing the stent along the guide catheter; a stent connecting member for connecting the stent with the pusher catheter; and a stent releasing member for releasing the stent from the pusher catheter by separating the connection between the stent and the pusher catheter depending on the stent connecting member, which is independently operable with relation to the guide catheter, and which is inserted into the inside of the pusher catheter.

The stent delivery system of the present invention may be arranged such that the stent connecting member is a flexible string, one end of which is fixed to the pusher catheter, the stent connecting member of which the one end is fixed to the pusher catheter is turned back in a state where the stent connecting member is engaged with the stent through the inside of the pusher catheter, the other end of the stent connecting member is turned back to reach the inside of the pusher catheter, and the stent releasing member maintains a state where the stent is connected with the pusher catheter by holding the other end of the stent connecting member in the inside of the pusher catheter, and allows separating of the stent from the pusher catheter by releasing the other end of the stent connecting member.

The stent delivery system of the present invention may be arranged such that a loop is formed at the other end of the stent connecting member, a high rigidity portion of which the rigidity is higher than that of the stent connecting member is disposed at a tip of the stent releasing member, and the high rigidity portion is detachably inserted into the loop.

The stent delivery system of the present invention may be arranged such that a hole is formed in the stent, and the stent connecting member is engaged with the stent by lacing the stent connecting member through the hole.

The stent delivery system of the present invention may be arranged such that the stent is provided with flaps for hooking the stent on the living body tissue, and the stent connecting member is engaged with the stent by hooking the stent connecting member on the flap.

The stent delivery system of the present invention may be arranged such that the hole of the stent is formed by notching a cylindrical wall of the stent so that the notch reaches the inside of the stent, and a circular cutout for preventing the stent from cracking of the notch is formed at the deepest portion of the notch.

The stent delivery system of the present invention may be arranged such that the stent connecting member is engaged with the stent so as to form like double loops.

The stent delivery system of the present invention may be arranged such that first and second holes are formed in a tube wall of the pusher catheter, the other end of the stent connecting member turned back is laced through the first hole from the inside of the pusher catheter toward the outside thereof, and the other end of the stent connecting member laced through the first hole is laced through the second hole from the outside of the pusher catheter toward the inside thereof.

The stent delivery system of the present invention may be arranged such that the stent releasing member is a wire made of resin or metal.

The stent delivery system of the present invention may be arranged such that the first hole is formed at a position of the pusher catheter which is closer to the tip thereof than the second hole, and the distance from the tip of the pusher catheter to the first hole is longer than the distance from the first hole to the second hole.

The stent delivery system of the present invention may be arranged such that the first hole is separate from the second hole in the longitudinal direction of the pusher catheter from the tip of the pusher catheter toward the terminal thereof, and the first and second holes are formed so that the holes are disposed at the position of the pusher catheter which is closer to the terminal thereof than a bending area of the pusher catheter.

The stent delivery system of the present invention may be arranged such that an operation portion grasped by an operator when the retracting the top end portion of the stent releasing member from the loop is performed, is disposed at the terminal of the stent releasing member, and the operation portion has a movable scope which is longer than the length of the top end portion of the stent releasing member protruding from the loop.

The stent delivery system of the present invention may be arranged such that the system further includes stoppers disposed on the movable scope, and which determine the moving of the operation portion so that the operation portion does not move over the movable scope.

The stent delivery system of the present invention may be arranged such that the stent connecting member is a flexible string, and one end of which is fixed to the pusher catheter, the stent connecting member of which one end is fixed to the pusher catheter is turned back in a state where the stent connecting member is engaged with the stent through the inside of the pusher catheter, the other end of the stent connecting member turned back is tied to the one end of the pusher catheter or to the stent connecting member with a unsnarlable knot, and the stent releasing member allows separating the stent from the pusher catheter by unsnarling the knot of the stent connecting member.

In the stent delivery system of the present invention, it is may be arranged such that the stent releasing member includes an engaging portion engaged with the knot, and the knot is unsnarled by pulling the engaging portion through the stent releasing member.

The stent delivery system of the present invention is for placing a cylindrically-shaped stent at a desired position within a living body, the system including: a guide catheter inserted into the inside of the stent, and inserted into the interior of the living body with the stent; a pusher catheter inserted into the interior of the living body with the guide catheter in a state where the guide catheter is inserted into the inside of the push catheter, and which is for pushing the stent along the guide catheter; a stent connecting member for connecting the stent with the pusher catheter; and a stent releasing member for releasing the stent from the pusher catheter by separating the connection between the stent and the pusher catheter depending on the stent connecting member, which is independently operable without relation to the guide catheter, and which is inserted into the inside of the pusher catheter; wherein the stent releasing member is inserted into the pusher catheter from the terminal of the pusher catheter toward the tip thereof so that the tip of the stent releasing member does not reach the top end of the pusher catheter.

DESCRIPTION OF THE PREFERRED EMBODIMENTS

A description is given of a first embodiment of the stent delivery system of the present invention with reference to FIG. 1 through FIG. 13.

Figure 1:
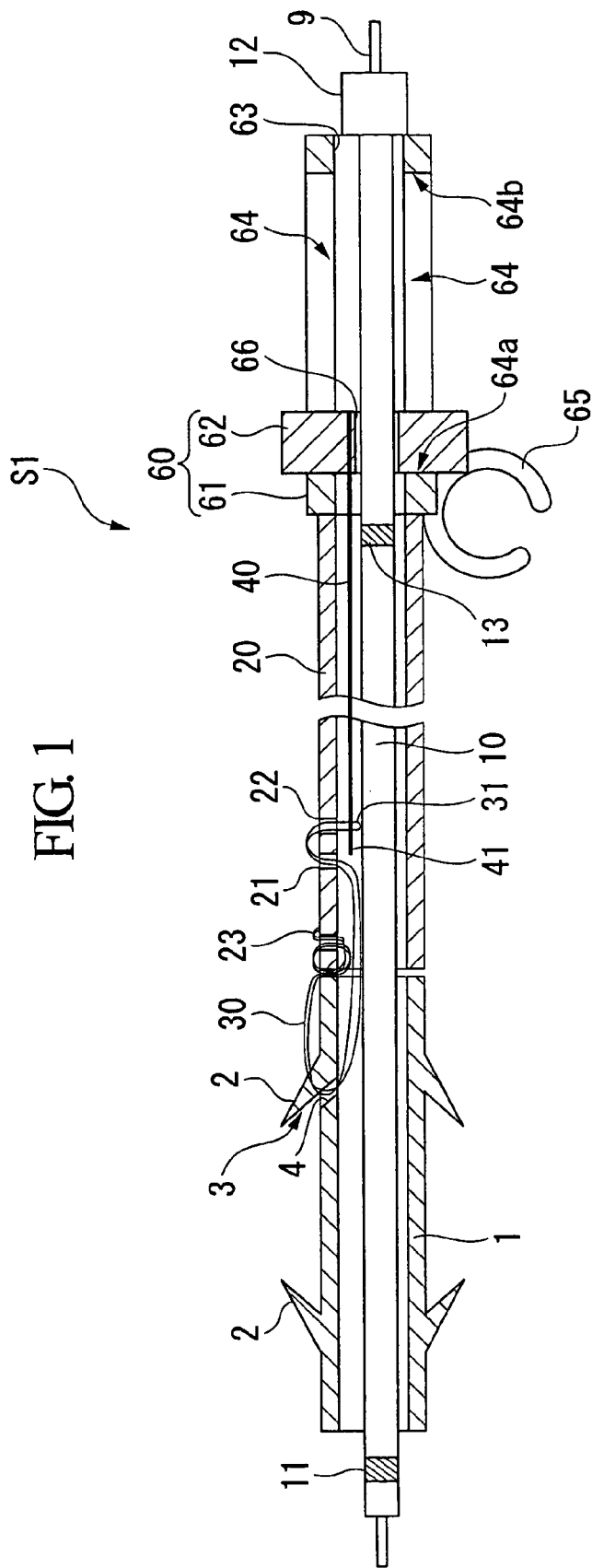
FIG. 1 is a sectional view showing a first embodiment of a stent delivery system of the present invention.

As shown in FIG. 1, a stent delivery system S1 of this embodiment includes a guide catheter 10, a pusher catheter 20, a stent connecting string (stent connecting member) 30, a stent releasing wire (stent releasing member) 40, and an operation section 60.

The guide catheter 10 is inserted into the inside of a stent 1, and is inserted into the interior of the living body with the stent 1 through a channel formed within an insertion portion of an endoscope. The pusher catheter 20 is inserted into the interior of the living body with the guide catheter 10 in a state where the guide catheter 10 is inserted into the inside of the pusher catheter 20, and pushes the stent 1 along the guide catheter 10. The stent connecting string 30 is used for connecting the stent 1 with the pusher catheter 20. The stent releasing wire 40 is independently operable without relation to the guide catheter 10. Also, the stent releasing wire 40 is inserted into the inside of the pusher catheter 20, and is used for releasing the stent 1 from the pusher catheter 20 by separating the engagement between the stent 1 and the pusher catheter 20 depending on the stent connecting string 30. The operation section 60 is used for operating the stent releasing wire 40.

Figure 2:
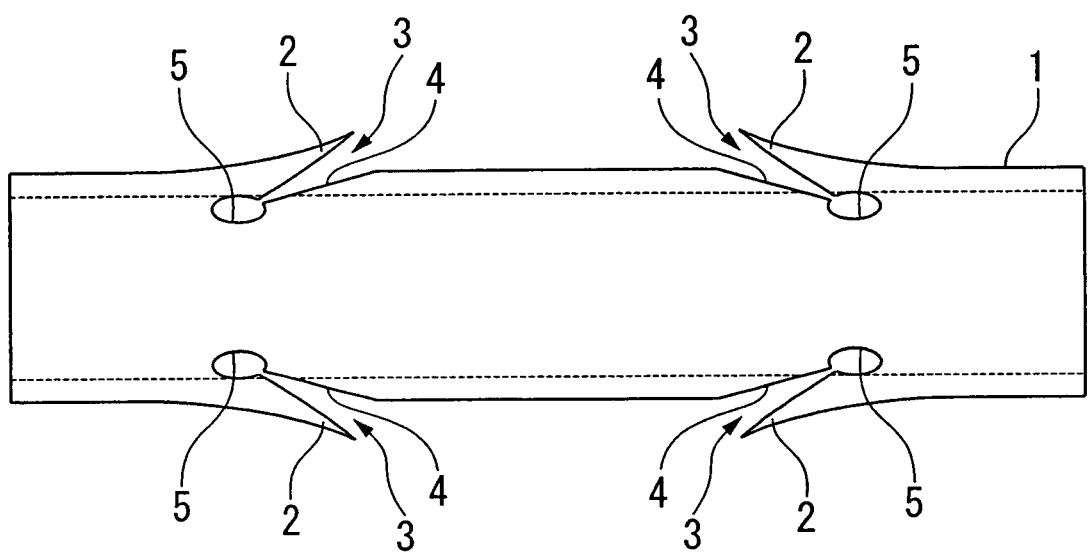
FIG. 2 is a side view showing a stent placed at the hollow organ using the stent delivery system of the first embodiment.

As shown in FIG. 2, the stent 1 placed at the interior of the living body by the stent delivery system S1 is made of resin or metal, and is formed like a cylinder. Flaps 2 are formed in both ends of the stent 1, and act as anchors for holding the stent 1 itself in place when the stent 1 is inserted into a stricture within the living body. Each of the flaps 2 is formed in a cylindrical wall of the stent 1 by forming a diagonal notch 3 which reaches the inside of the stent 1. A sharp tongue piece formed by the notch 3 forms the flap 2 as an anchor. Small holes 4 penetrating the cylindrical wall from the outside surface to the inside surface are formed in the cylindrical wall of the stent 1. The small hole 4 is used when the stent connecting string 30 is engaged with the stent 1. Circular cutouts 5 are formed at the deepest portion of the notch 3. The cutouts 5 prevent the cylindrical wall of the stent 1 from breaking of the notch 3.

As shown in FIG. 1, the guide catheter 10 is made of resin, and is formed like a flexible and long tube. The internal diameter of the guide catheter 10 is a predetermined size so that a guide wire (guide member) 9 can be detachably inserted to the inside of the guide catheter 10.

A contrasting portion 11 for easily contrasting a head section of the guide catheter 10 under X-ray illumination is disposed at the head section of the guide catheter 10. A sleeve 12 grasped by an operator when the guide catheter 10 is operated, is disposed at the base end of the guide catheter 10. Further, an indicator 13 is disposed on the outside surface of a part of the guide catheter 10 which is close to the sleeve 12. The indicator 13 is used for allowing the operator to recognize the pulling amount of the guide catheter 10 by highlighting the position of the guide catheter 10 with respect to the pusher catheter 20.

The pusher catheter 20 is made of resin, and is formed like a flexible and long tube similar to the guide catheter 10. The internal diameter of the pusher catheter 20 is a predetermined size so that the guide catheter 10 can be detachably inserted to the inside of the pusher catheter 20, and the stent releasing wire 40 can be detachably inserted between the inside surface of the pusher catheter 20 and the outside surface of the guide catheter 10.

Two holes (first and second hole) 21 and 22 used for connecting the stent 1 with the pusher catheter 20 are formed at the head section thereof. The holes 21 and 22 are disposed at the position which is closer to the base end of the pusher catheter 20 than an area in which the pusher catheter 20 is bent when the pusher catheter 20 protrudes from the tip of the insertion portion of the endoscope. Further, the hole 21 is separate from the hole 22 in the longitudinal direction of the pusher catheter 20 from the tip of the pusher catheter 20 toward the terminal thereof, and the hole 21 is formed at the position which is closer to the tip of the pusher catheter 20 than the hole 22. Furthermore, the distance from the tip end surface of the pusher catheter 20 to the hole 21 is longer than the distance to the hole 22 from the hole 21.

Separate from the two holes 21 and 22 as mentioned above, a hole 23 used for connecting one end of the stent connecting string 30 with the pusher catheter 20 is formed at the head section thereof. The hole 23 is disposed closer to the tip of the pusher catheter 20 than the hole 21, and is disposed in the vicinity of the tip of the pusher catheter 20. The operation section 60 as mentioned below is disposed at the terminal of the pusher catheter 20.

The stent connecting string 30 is made of resin or silk, and both ends of which are laced through the hole 23 and are tied or adhered to the pusher catheter 20. Therefore, the stent connecting string 30 has a loop. Hereunder, a part of the stent connecting string 30 tied (or adhered) to the pusher catheter 20 forms one end of the stent connecting string 30, and a part of the stent connecting string 30 which is furthest from the one end forms the other end of the stent connecting string 30. A loop 31 is formed at the other end of the stent connecting string 30.

The stent connecting string 30 connects the stent 1 with the pusher catheter 20 as below. First, the stent 1 is disposed at the tip of the pusher catheter 20 so that the inside space of the stent 1 is in communication with the inside space of the pusher catheter 20. Next, the stent connecting string 30 is inserted into the inside of the pusher catheter 20, and is led out from between the pusher catheter 20 and the stent 1 to the outside. Next, the stent connecting string 30 led out is laced through the small hole 4 of the stent 1 from the outside of the stent 1 to the inside thereof, and is turned back toward the pusher catheter 20. Next, the stent connecting string 30 turned back is inserted into the inside of the stent 1 and the inside of the pusher catheter 20, and is laced through the hole 21 from the inside of the pusher catheter 20 to the outside thereof. Next, the other end of the stent connecting string 30 led out to the outside of the pusher catheter 20 through the hole 21 and is laced through the hole 22 of the pusher catheter 20 from the outside of the pusher catheter 20 to the inside thereof. The loop 31 formed at the other end of the stent connecting string 30 is disposed at the inside of the pusher catheter 20, and is held by a top end portion 41 of the stent releasing wire 40.

The stent releasing wire 40 is made of resin or metal, and is inserted between the inside surface of the pusher catheter 20 and the outside surface of the guide catheter 10 inserted to the inside of the pusher catheter 20 from the terminal of the pusher catheter 20 toward the tip thereof so that the tip of the stent releasing wire 40 reaches the hole 22 and does not reach the tip of the pusher catheter 20. The rigidity of the stent releasing wire 40 everywhere in the body thereof is higher than that of the stent connecting string 30. That is, the top end portion 41 of the stent releasing wire 40 is a high rigidity portion which is more rigid than the stent connecting string 30, and is inserted into the loop 31 formed at the other end of the stent connecting string 30 disposed at the inside of the pusher catheter 20.

In a state where the top end portion 41 of the stent releasing wire 40 is inserted into the loop 31 formed at the other end of the stent connecting string 30, since the top end portion 41 of the stent releasing wire 40 is the key, it prevents the stent connecting string 30 from dropping out from the hole 22 of the pusher catheter 20. Note that, the high rigidity portion may be formed at the top end of the stent releasing wire 40, and the rigidity of the other part of the top end of the stent releasing wire 40 may be lower than the stent connecting string 30.

The stent releasing wire 40 maintains the connection of the stent 1 with the pusher catheter 20 by holding the loop 31 formed at the other end of the stent connecting string 30 by the top end portion 41 of the stent releasing wire 40, and allows the stent 1 to be separated from the pusher catheter 20 by releasing the loop 31 from the top end portion 41.

The operation section 60 includes a base portion 61 and an operation section main body (operation portion) 62 grasped by the operator when the retracting operation of the top end portion 41 of the stent releasing wire 40 from the loop 31 is performed. A hook 65 for hooking the operation section 60 on the endoscope is disposed on the base portion 61.

The base portion 61 is made of solid resin, and is formed like a cylinder. Also, the base portion 61 is disposed at the terminal of the pusher catheter 20 so that a hole 63 formed at the inside of the base portion 61 is in communication with the inside space of the pusher catheter 20. Each of two slits 64 is formed in a cylindrical wall of the base portion 61 so that the slit extends in the longitudinal direction of the base portion 61. The two slits 64 are formed so as to separate each other in the width direction of the base portion 61. The operation section main body 62 is inserted into the two slits 64, and is slidable along the slits 64 in the longitudinal direction of the slits 64. That is, the operation section main body 62 is slidable in the longitudinal direction of the pusher catheter 20 continuing to the base portion 61.

The operation section main body 62 is connected with the terminal of the stent releasing wire 40. The stent releasing wire 40 is moved by sliding the operation section main body 62 along the slits 64. A hole 66 is formed in the middle of the operation section main body 62, and the guide catheter 10 is inserted into the hole 66. The internal diameter of the hole 66 is larger than the external diameter of the guide catheter 10. Therefore, the operation section main body 62 is movable while being constrained by the guide catheter 10.

The length of the slit 64 is made of a predetermined size so that the movable scope of the operation section main body 62 is larger than the length of the top end portion 41 of the stent releasing wire 40 protruding from the loop 31. Therefore, two wall surfaces 64a and 64b which face each other at a distance in the longitudinal direction of the slit 64 act as stoppers on the movable scope, and regulate the moving of the operation section main body 62 so that the operation section main body 62 does not move over the movable scope.

In a state where the operation section main body 62 contacts to the wall surface 64a of the slit 64, the top end portion 41 of the stent releasing wire 40 is inserted into the loop 31 formed at the other end of the stent connecting string 30. In a state where the operation section main body 62 contacts to the wall surface 64b of the slit 64, the top end portion 41 of the stent releasing wire 40 is reliably retracted away from the loop 31 formed at the other end of the stent connecting string 30. Initially, the operation section main body 62 contacts to the wall surface 64a.

A description is given of a procedure of an operation for placing the stent at a stricture of the biliary tract using the stent delivery system S1 constructed as mentioned above.

Figure 3:
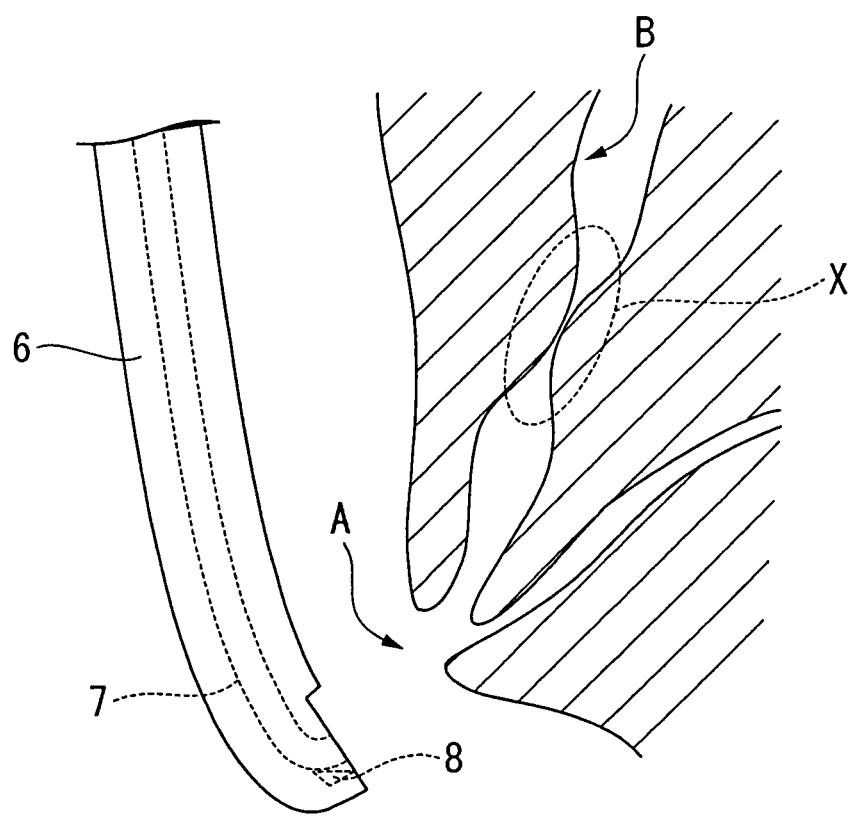
FIG. 3 is a view for depicting the procedure of the operation performed using the stent delivery system of the first embodiment, and shows a state where the head section of the insertion portion of the endoscope is disposed in the vicinity of the duodenal papilla.

In the operation, first, as shown in FIG. 3, an insertion portion 6 of an endoscope is inserted into the interior of a living body, then a tip of the insertion portion 6 reaches the vicinity of a duodenal papilla A. Note that, a lateral vision type endoscope is used with this operation. A standing block 8 is disposed at the tip of the insertion portion 6 of the endoscope so as to be close to an opening of a channel 7. The standing block 8 curves an instrument protruding from the tip of the insertion portion 6 so as to adjust the protruding angle of the instrument by moving of the standing block 8. The standing block 8 is moved by operating an operation section (not illustrated) disposed at a base section of the endoscope.

Figure 4:
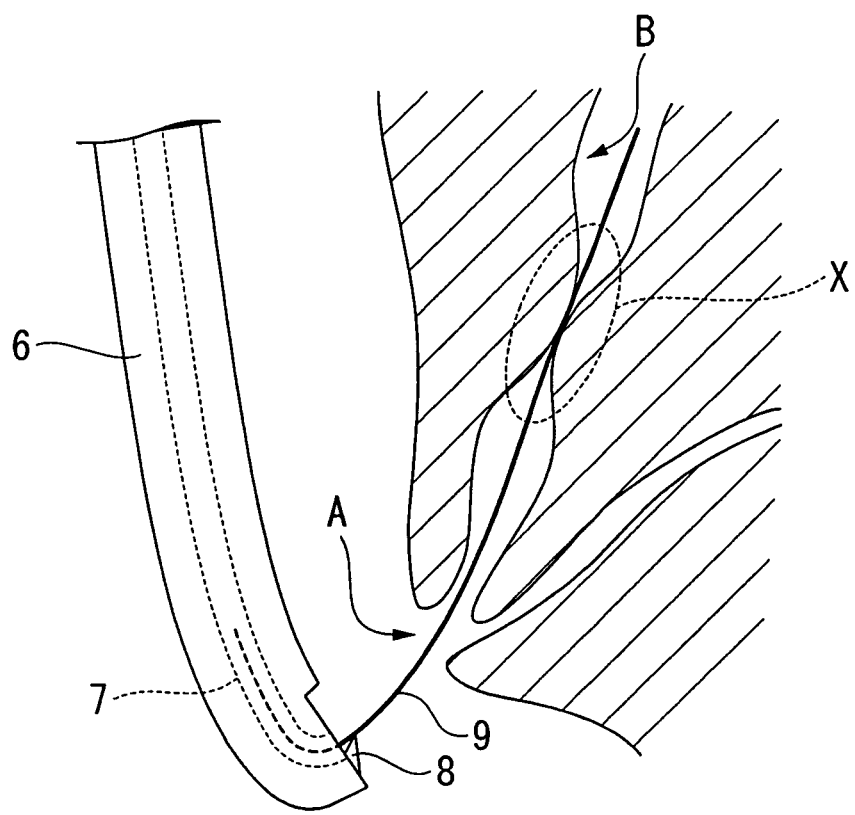
FIG. 4 is a view for depicting the procedure of the operation performed using the stent delivery system of the first embodiment, and shows a state where the guide wire is inserted into the stricture of the biliary tract.

Next, a cannula is inserted into the channel 7 of the insertion portion 6, then the cannula is protruded from the tip of the insertion portion 6. The cannula is curved by the standing block 8, then a head section of the cannula is inserted into a biliary tract B. A contrast agent is introduced into the biliary tract B through the cannula. After introducing the contrast agent, the guide wire 9 is inserted into a stricture X of the biliary tract B through the cannula. Thereafter, as shown in FIG. 4, the cannula is retracted away from the biliary tract B and the channel 7 while leaving only the guide wire 9.

Figure 5:
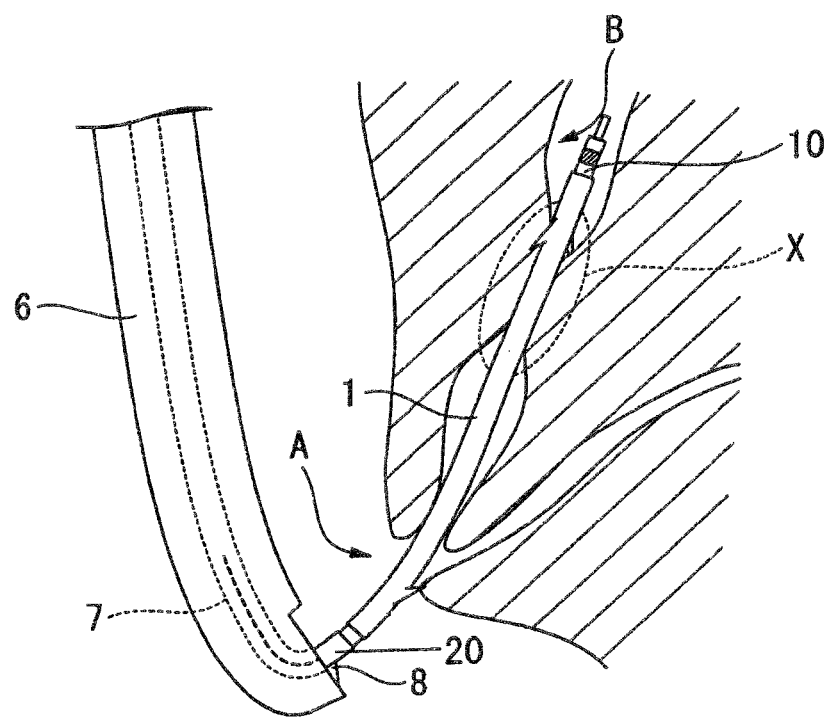
FIG. 5 is a view for depicting the procedure of the operation performed using the stent delivery system of the first embodiment, and shows a state where the stent and the guide catheter are inserted into the stricture.

Next, the five members joined as shown in FIG. 1, that is, the stent 1, the guide catheter 10, the pusher catheter 20, the stent connecting string 30 and the stent releasing wire 40 are inserted into the channel 7 along the guide wire 9, then the members are protruded from the tip of a insertion portion 6. The guide catheter 10 and the pusher catheter 20 are curved by the standing block 8, as shown in FIG. 5, and the stent 1 and the guide catheter 10 are inserted into the stricture X.

Figure 7:
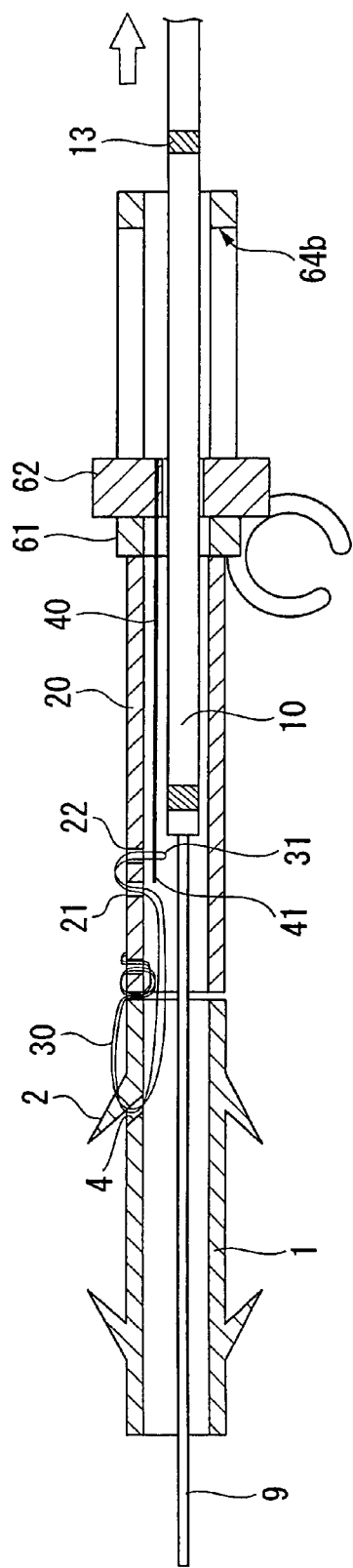
FIG. 7 is a view for depicting the procedure of the operation performed using the stent delivery system of the first embodiment, and shows a state where the guide catheter is retracted.

Next, as shown in FIG. 7, in a state where the guide wire 9 and the pusher catheter 20 are held in place, the guide catheter 10 is retracted by pulling the guide catheter 10 so as to retract it from the channel 7 of the insertion portion 6 of the endoscope. At this time, it is not always necessary to retract the full length of the guide catheter 10. The operator may cause relative movement of the guide catheter 10 with respect to the pusher catheter 20 using an indicator 13 as a target. When the guide catheter 10 is pulled until the indicator 13 becomes exposed from the terminal end of the base portion 61, the head section of the guide catheter 10 is retracted away from the stent 1, and then retracts to the inside of the pusher catheter 20 until the head portion of the guide catheter 10 is closer to the terminal of the pusher catheter 20 than the hole 22.

Figure 8:
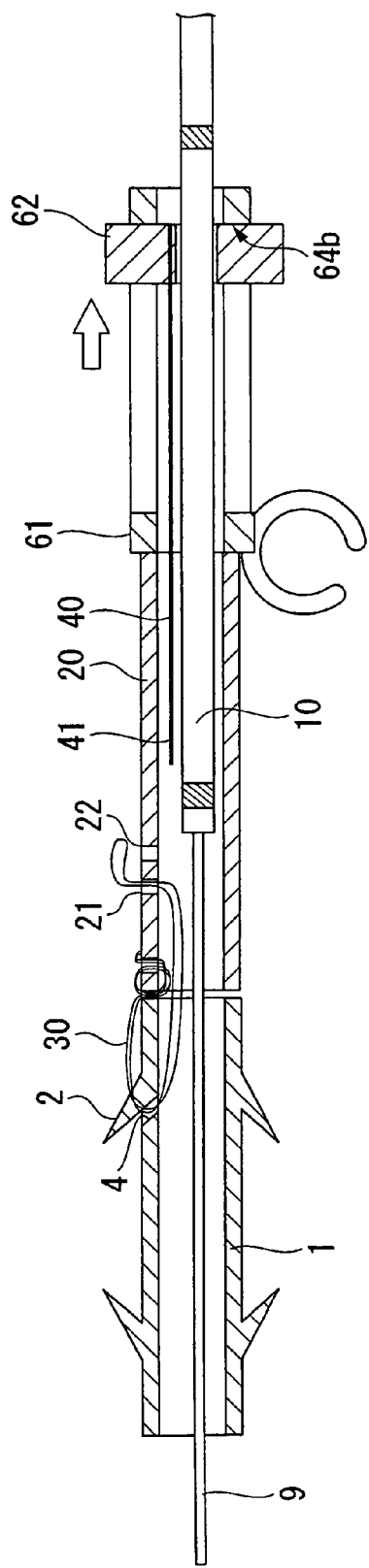
FIG. 8 is a view for depicting the procedure of the operation performed using the stent delivery system of the first embodiment, and shows a state where the top end portion of the stent releasing wire is retracted away from the loop of the stent connecting string.

Next, as shown in FIG. 8, in a state where the guide wire 9 and the pusher catheter 20 are held in place, the operation section main body 62 is moved until the operation section main body 62 contacts to the wall surface 64b. Accordingly, the top end portion 41 of the stent releasing wire 40 is retracted away from the loop 31 formed at the other end of the stent connecting string 30, and the constraint of the stent 1 by the stent connecting string 30 is eliminated. That is, the engagement between the stent 1 and the pusher catheter 20 through the stent connecting string 30 is separated.

Figure 6:
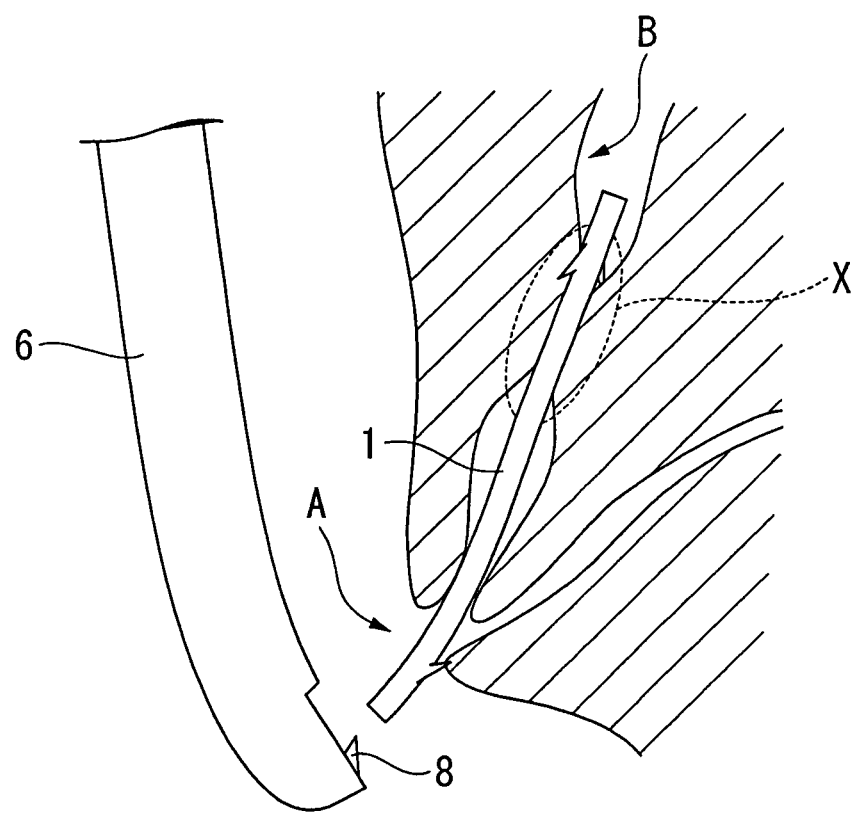
FIG. 6 is a view for depicting the procedure of the operation performed using the stent delivery system of the first embodiment, and shows a state where only the stent is placed at the stricture.
Figure 9:
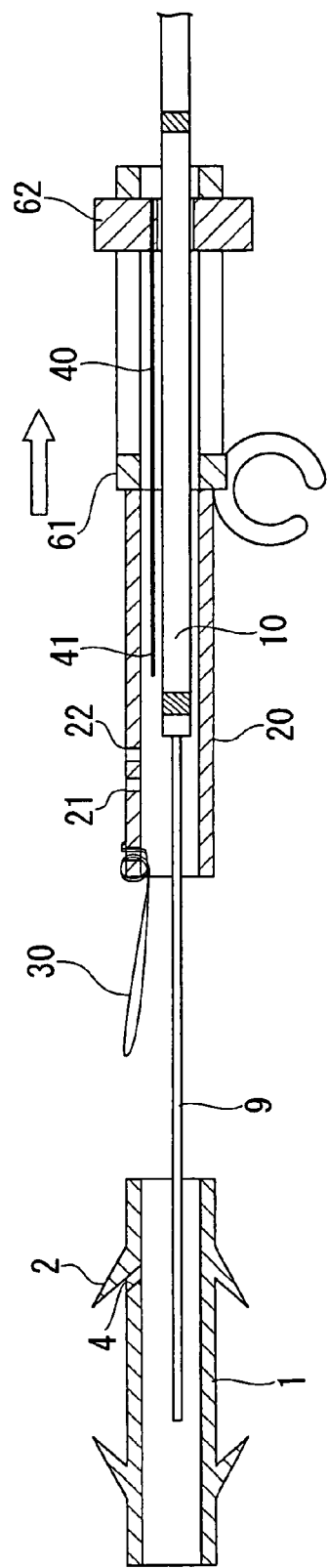
FIG. 9 is a view for depicting the procedure of the operation performed using the stent delivery system of the first embodiment, and shows a state where the pusher catheter is retracted.

Next, as shown in FIG. 9, when the pusher catheter 20 is retracted by pulling the pusher catheter 20 so as to retract it from the channel 7 of the insertion portion 6 of the endoscope, since the constraint of the stent 1 by the stent connecting string 30 has been eliminated already, the pusher catheter 20 separates from the stent 1 gradually. In the process, the stent connecting string 30 is retracted from the holes 21 and 22 of the pusher catheter 20, and the string is also retracted from the small hole 4 of the stent 1. Finally, as shown in FIG. 6, only the stent 1 is placed at the stricture X.

With the operation as mentioned above, when the stent 1 and the head section of the guide catheter 10 are inserted into the stricture X, if the stent 1 is placed at a position which is deeper than the stricture X, the pusher catheter 20 is pulled slightly before separating the engagement between the stent 1 and the pusher catheter 20. Therefore, it is possible to replace the stent 1 connected with the tip of the pusher catheter 20 to the desired position. In this embodiment, the stent 1 may be replaced at an accurate position before the guide catheter 10 or the guide wire 9 are retracted, otherwise it may be replaced after the guide catheter 10 or the guide wire 9 has been retracted.

According to the stent delivery system S1 constructed as mentioned above, the stent releasing wire 40 which is independently operable without relation to the guide catheter 10 is inserted into the inside of the pusher catheter 20. Therefore, it is possible to separate the engagement between the stent 1 and the pusher catheter 20 by operating the stent releasing wire 40. As a result, if the guide catheter 10 has been retracted already, it is possible to replace the stent 1 at the accurate position.

Since the stent connecting string 30 is engaged with the stent 1 through the inside of the pusher catheter 20, if the stent 1 and the head section of the pusher catheter 20 protrude from the tip of the insertion portion 6 of the endoscope, the stent connecting string 30 never catches on the standing block 8 disposed at the tip of the insertion portion 6.

By retracting the stent releasing wire 40 from the loop 31 of the stent connecting string 30, the engagement between the stent 1 and the pusher catheter 20 through the stent connecting string 30 is separated. Therefore, the releasing operation of the stent 1 can easily be performed.

Since the stent releasing wire 40 is made of resin or metal, a frictional force between the stent releasing wire 40 and the pusher catheter 20 or between the stent releasing wire 40 and the guide catheter 10 is smaller than that of a stent releasing system by pulling the guide catheter such as the stent delivery system disclosed in the document of U.S. Pat. No. 5,921,952. Therefore, only slight pulling of the stent releasing wire 40 is required.

Since the hole 21 is separate from the hole 22 in the longitudinal direction of the pusher catheter 20 from the tip of the pusher catheter 20 toward the terminal thereof, the top end portion 41 of the stent releasing wire 40 is not inserted into a bent area of the pusher catheter 20. Thus, when the head section neighborhood of the pusher catheter 20 is bent, since the stent releasing wire 40 is not inserted into the top end neighborhood, the stent releasing wire 40 is not bent. Therefore, while the stent releasing wire 40 is retracted away from the pusher catheter 20, a frictional force caused by an elastic force of the stent releasing wire 40 is slight. As a result, it is possible to operate the stent releasing wire 40 with a slight force.

Since the movable scope of the operation section main body 62 is distinctly larger than the length of the top end portion 41 of the stent releasing wire 40 protruding from the loop 31, when the operation section main body 62 is operated, the top end portion 41 of the stent releasing wire 40 is reliably retracted away from the loop 31. Therefore, the operator can release only to operate the operation section main body 62 at the full of the movable scope without a thought. As a result, it is possible to reduce a work burden of the operator.

Figure 10:
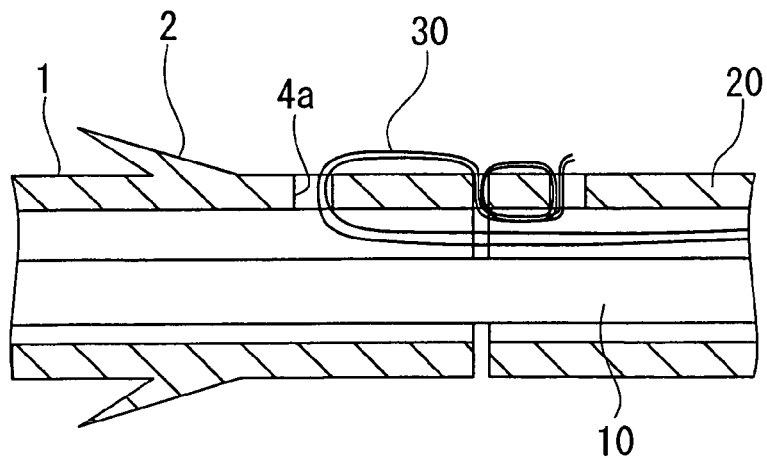
FIG. 10 is a sectional view showing a substantial part of a variant relating to the stent of the first embodiment.
Figure 11:
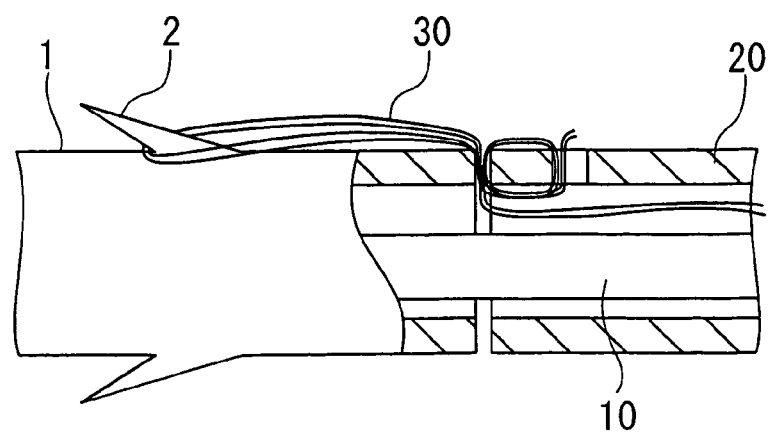
FIG. 11 is a sectional view showing a substantial part of another variant relating to the stent of the first embodiment.

With this embodiment, each of the small holes is formed in the stent 1 by forming the notch 3 in the cylindrical wall of the stent 1, and the stent connecting string 30 is laced through the small hole 4. However, as shown in FIG. 10, the stent connecting string 30 may be laced through a small hole 4a formed in the cylindrical wall of the stent 1 without the notch 3. In this case, the flap 2 may not be formed by the notch 3. In addition, for example, as shown in FIG. 11, the stent connecting string 30 may be hooked on the flap 2 of the stent 1 without the small hole 4.

Further, with this embodiment, the stent connecting string 30 is tied (or adhered) to the tip of the pusher catheter 20 so as to form like a ring, and a loop formed by a part of the ring is engaged with the stent 1. However, the stent connecting string 30 may be engaged with the stent 1 so as to form like the double loops previously.

Figure 12:
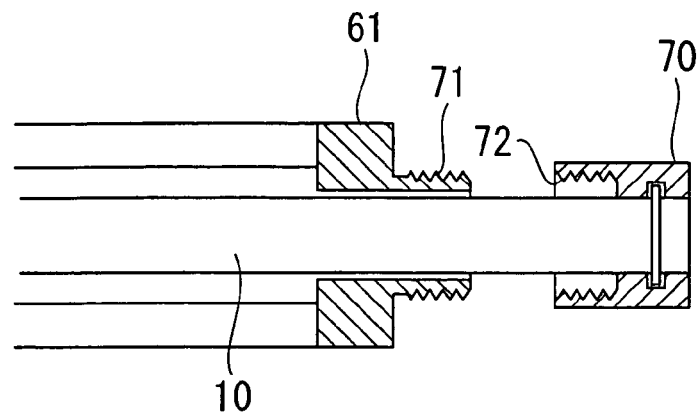
FIG. 12 is a sectional view showing a substantial part of a variant relating to the stent delivery system of the first embodiment.

With this embodiment, the guide catheter 10 may be fixable to the pusher catheter 20. That is, as shown in FIG. 12, a sleeve 70 grasped by the operator when he operates the guide catheter 10 is disposed at the terminal of the guide catheter 10. A male screw 71 protruding toward the sleeve 70 is formed on the base portion 61 being with respect to the sleeve 70. On the contrary, a female screw 72 screwed the male screw 71 of the base portion 61 is formed in the sleeve 70. With this embodiment, when the guide catheter 10 is fixed to the pusher catheter 20 by screwing the male screw 71 into the female screw 72, it is possible to operate the guide catheter 10 together with the pusher catheter 20. When the male screw 71 is separated from the female screw 72, it is possible to operate the guide catheter 10 separately from the pusher catheter 20.

Figure 13:
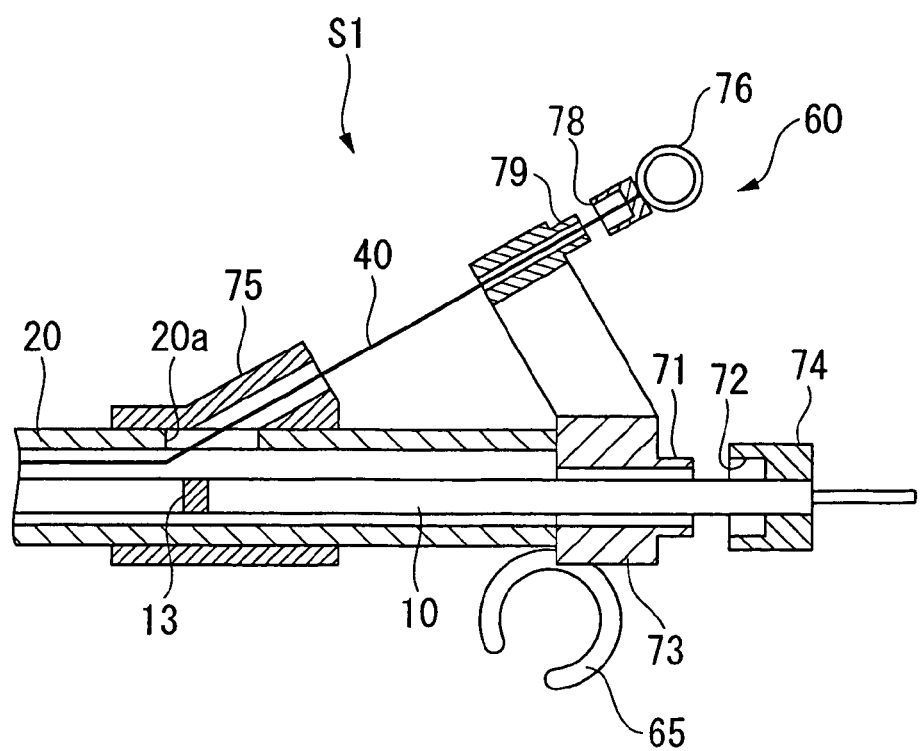
FIG. 13 is a sectional view showing a substantial part of another variant relating to the stent delivery system of the first embodiment.

With this embodiment, the operation section 60 may be constructed as below. That is, as shown in FIG. 13, the base end of the pusher catheter 20 is provided with a base portion 73, and a sleeve 74 grasped by the operator when he operates the guide catheter 10. The male screw 71 is formed on the base portion 73 being with respect to the sleeve 74. On the contrary, the female screw 72 screwed the male screw 71 of the base portion 73 is formed in the sleeve 74. Similarly to the above description, it is possible to operate the guide catheter 10 together with the pusher catheter 20, or separately from the pusher catheter 20.

Further, a bifurcation member 75 which separates the base end of the stent releasing wire 40 from the pusher catheter 20 is disposed at a part of the pusher catheter 20 which is closer to the tip of the pusher catheter 20 than the base portion 73. The terminal of the stent releasing wire 40 is led out to the exterior of the pusher catheter 20 through a through-hole 20a formed in a tube wall of the pusher catheter 20. A wire releasing ring 76 grasped by the operator when he operates the stent releasing wire 40 is attached to the terminal of the stent releasing wire 40. The wire releasing ring 76 is movably supported by a releasing wire support portion 77 integrally-formed on the base portion 73 in a retraction direction of the stent releasing wire 40. A female screw 78 is formed in the wire releasing ring 76, and a male screw 79 screwed into the female screw 78 is formed on the releasing wire support portion 77. It is possible to attach the wire releasing ring 76 to the releasing wire support portion 77 when the need does not arise.

A description is given of a second embodiment of the stent delivery system of the present invention with reference to FIG. 14 through FIG. 18. Note that, the same descriptive symbols are used for component elements that are the same as those used in the first embodiment and a description thereof is omitted.

Figure 14:
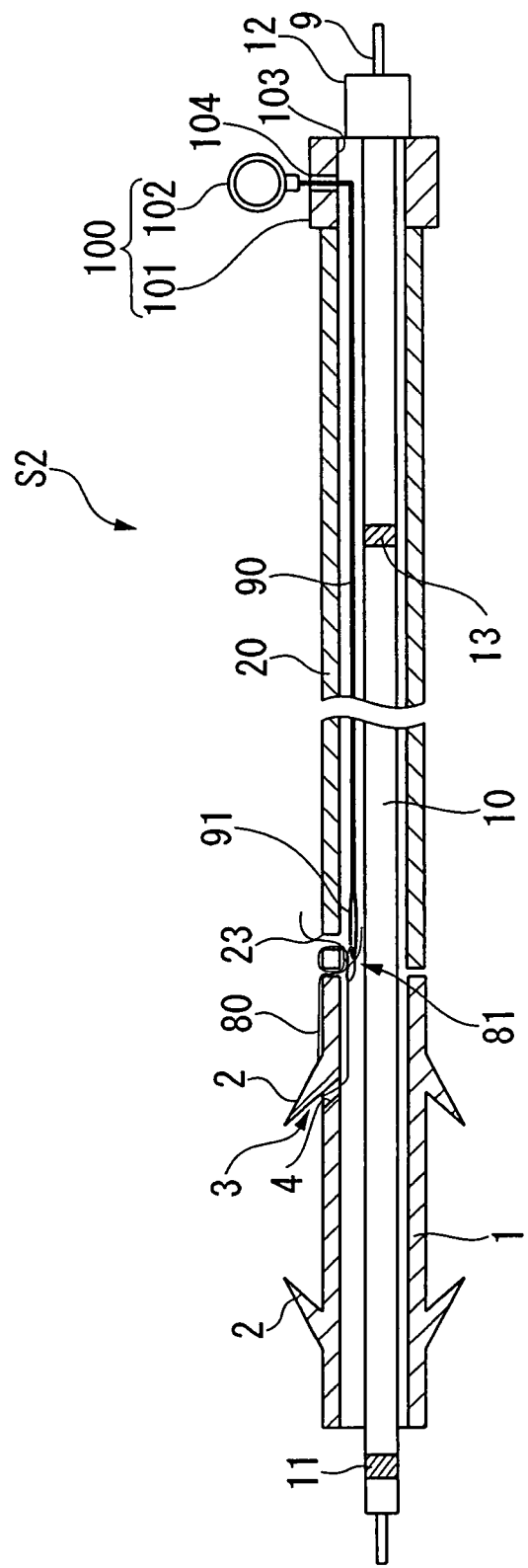
FIG. 14 is a sectional view showing a second embodiment of a stent delivery system of the present invention.

As shown in FIG. 14, the stent delivery system S2 of this embodiment includes a guide catheter 10, a pusher catheter 20, a stent connecting string (stent connecting member) 80, a stent releasing wire (stent releasing member) 90, and an operation section 100.

The stent connecting string 80 is made of resin or silk, one end of which is laced through the hole 23 of the pusher catheter 20 and is tied or adhered to the pusher catheter 20. Differently from the first embodiment, the pusher catheter 20 is not provided with the holes 21 and 22.

Figure 15:
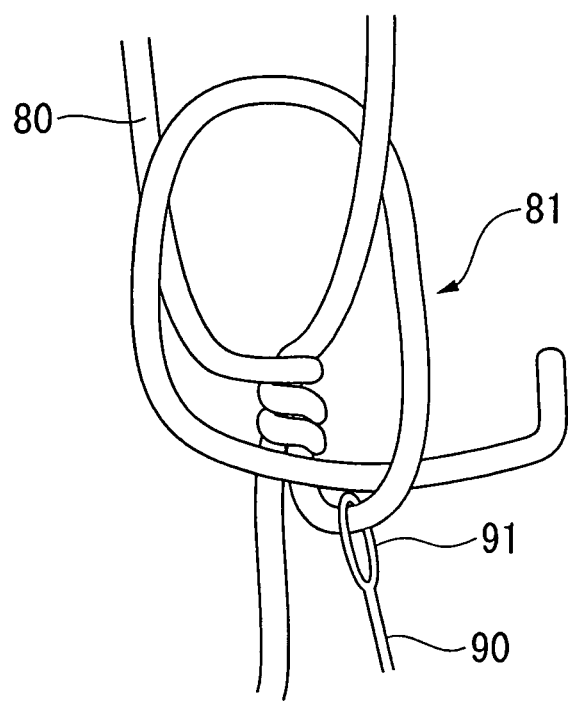
FIG. 15 is a view showing the stent connecting member of the second embodiment.

The stent connecting string 80 connects the stent 1 with the pusher catheter 20 as below. First, the stent 1 is disposed at the tip of the pusher catheter 20 so that the inside space of the stent 1 is in communication with the inside space of the pusher catheter 20. Next, the stent connecting string 80 is inserted into the inside of the pusher catheter 20, and is led out from between the pusher catheter 20 and the stent 1 to the outside. Next, the stent connecting string 80 led out is laced through the small hole 4 of the stent 1 from the outside of the stent 1 to the inside thereof, and is turned back toward the pusher catheter 20. Next, the other end of the stent connecting string 80 turned back is tied to the one end thereof with a unsnarlable knot, for example, as shown in FIG. 15, a clinch knot. The stent releasing wire 90 allows the stent 1 to be separated from the pusher catheter 20 by unsnarling the knot 81 of the stent connecting string 80. Note that, the other end of the stent connecting string 80 may also be tied to the pusher catheter 20 instead of one end of the stent connecting string 80 with the unsnarlable knot as mentioned above.

The stent releasing wire 90 is made of resin or metal, and is inserted between the inside surface of the pusher catheter 20 and the outside surface of the guide catheter 10 inserted to the inside of the pusher catheter 20. A loop (engaging portion) 91 engaged with the knot 81 is formed at a tip of the stent releasing wire 90. The knot 81 of the stent connecting string 80 is unsnarled by pulling the loop 91 through the stent releasing wire 90.

In a state where the other end of the stent connecting string 80 is tied to the one end the stent connecting string 80, the stent connecting string 80 is prevented from dropping out from the small hole 4 of the stent 1. Unless the stent connecting string 80 drops out from the small hole 4, the stent connecting string 80 keeps holding the stent 1.

The operation section 100 includes a base portion 101, and a wire releasing ring (operation portion) 102 grasped by the operator when he pulls the loop 91 through the stent releasing wire 90.

The base portion 101 is made of solid resin, and is formed like a cylinder. Also, the base portion 101 is disposed at the base end of the pusher catheter 20 so that a hole 103 formed at the inside of the base portion 101 is in communication with the inside space of the pusher catheter 20. A small hole 104 communicating to the hole 103 is formed in a wall of the base portion 101 in the radial direction of the base portion 101. The other end of the stent releasing wire 90 is inserted into the small hole 104. The wire releasing ring 102 is fixed to the other end of the stent releasing wire 90 protruding from the small hole 104.

A description is given of a procedure of an operation for placing the stent at a stricture of the biliary tract using the stent delivery system S2 constructed as mentioned above.

In the operation, first, the insertion portion 6 of the endoscope is inserted into the interior of the living body, then the tip of the insertion portion 6 reaches the vicinity of the duodenal papilla A (refer to FIG. 3).

Next, a cannula is inserted into the channel 7 of the insertion portion 6, and then the cannula is protruded from the tip of the insertion portion 6. The cannula is curved by the standing block 8, and then a head section of the cannula is inserted into the biliary tract B. A contrast agent is introduced into the biliary tract B through the cannula. After introducing the contrast agent, the guide wire 9 is inserted into a stricture X of the biliary tract B through the cannula. Thereafter, the cannula is retracted away from the biliary tract B and the channel 7 while leaving only the guide wire 9 (refer to FIG. 4).

Next, the five members joined as shown in FIG. 14, that is, the stent 1, the guide catheter 10, the pusher catheter 20, the stent connecting string 80 and the stent releasing wire 90 are inserted into the channel 7 along the guide wire 9, and then the members are protruded from the tip of a insertion portion 6. The guide catheter 10 and the pusher catheter 20 are curved by the standing block 8, and the stent 1 and the guide catheter 10 are inserted into the stricture X (refer to FIG. 5).

Figure 16:
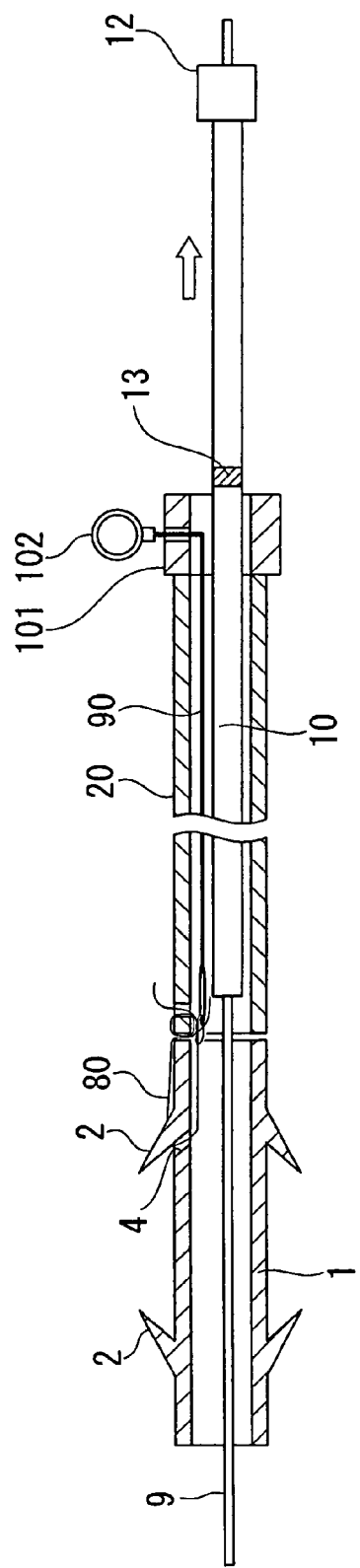
FIG. 16 is a view for depicting the procedure of the operation performed using the stent delivery system of the second embodiment, and shows a state where the guide catheter is retracted.

Next, as shown in FIG. 16, in a state where the guide wire 9 and the pusher catheter 20 are held in place, the guide catheter 10 is retracted by pulling the guide catheter 10 so as to retract it from the channel 7 of the insertion portion 6 of the endoscope. At this time, it is not always necessary to retract away the full length of the guide catheter 10. The operator may cause relative movement of the guide catheter 10 with respect to the pusher catheter 20 using an indicator 13 as a target. When the guide catheter 10 is pulled until the indicator 13 becomes exposed, the head section of the guide catheter 10 is retracted away from the stent 1, and retracts to the inside of the pusher catheter 20.

Figure 17:
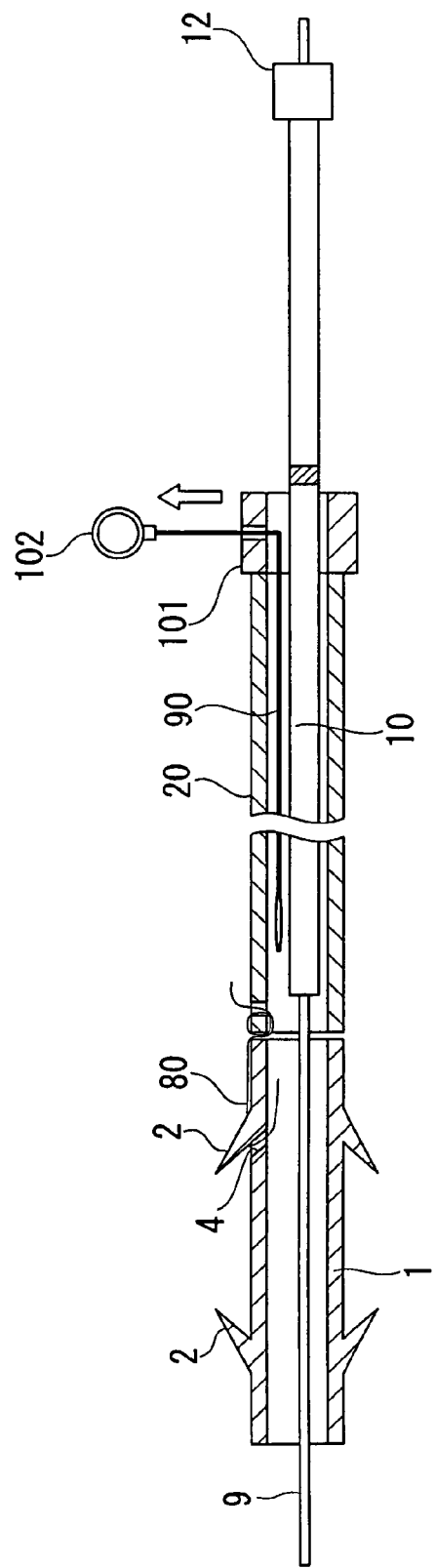
FIG. 17 is a view for depicting the procedure of the operation performed using the stent delivery system of the second embodiment, and shows a state where the stent connecting member is released by using the stent releasing wire.

Next, as shown in FIG. 17, in a state where the guide wire 9 and the pusher catheter 20 are held in place, the wire releasing ring 102 is pulled. Accordingly, the knot 81 of the stent connecting string 80 is unsnarled by the loop 91 formed at the tip of the stent releasing wire 90, and the constraint of the stent 1 by the stent connecting string 80 is eliminated. That is, the engagement between the stent 1 and the pusher catheter 20 through the stent connecting string 80 is separated.

Figure 18:
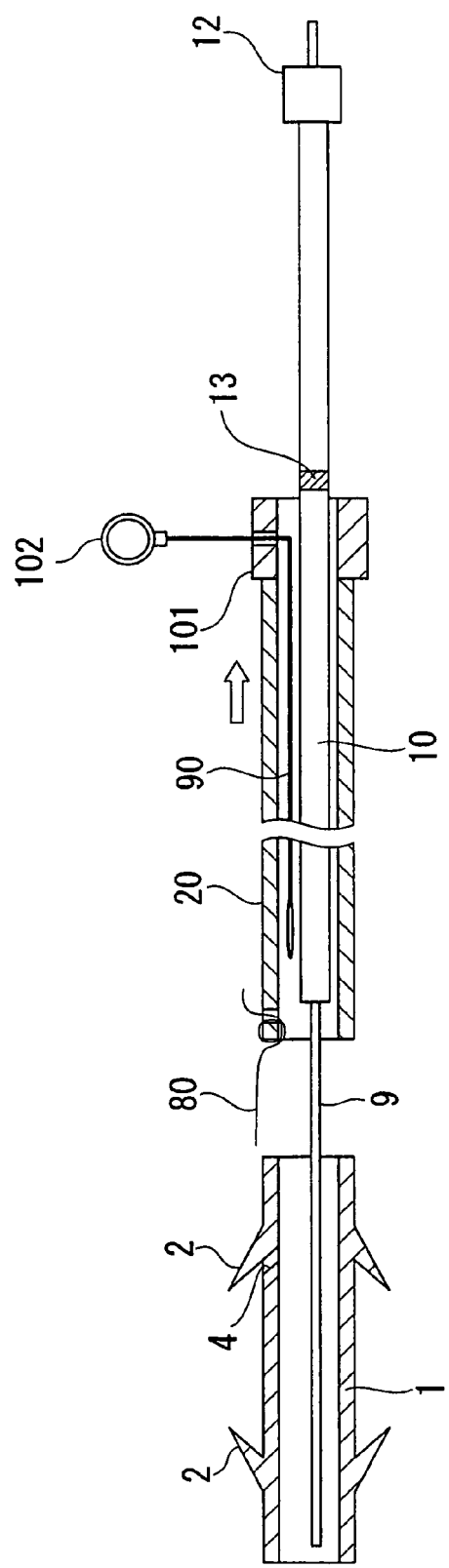
FIG. 18 is a view for depicting the procedure of the operation performed using the stent delivery system of the second embodiment, and shows a state where the pusher catheter is retracted.

Next, as shown in FIG. 18, when the pusher catheter 20 is retracted by pulling the pusher catheter 20 so as to retract it from the channel 7 of the insertion portion 6 of the endoscope, since the constraint of the stent 1 by the stent connecting string 80 has been eliminated already, the pusher catheter 20 separates from the stent 1 gradually. In the process, the stent connecting string 80 is retracted from the small hole 4 of the stent 1. Finally, only the stent 1 is placed at the stricture X (refer to FIG. 6).

With the operation as mentioned above, when the stent 1 and the head section of the guide catheter 10 are inserted into the stricture X, if the stent 1 is placed at a position which is deeper than the stricture X, the pusher catheter 20 is pulled slightly before separating the engagement between the stent 1 and the pusher catheter 20. Therefore, it is possible to replace the stent 1 connected with the tip of the pusher catheter 20 to the desired position. In this embodiment, the stent 1 may be replaced at an accurate position before the guide catheter 10 or the guide wire 9 are retracted, otherwise it may be replaced after the guide catheter 10 or the guide wire 9 has been retracted.

According to the stent delivery system S2 constructed as mentioned above, the stent releasing wire 90 which is independently operable separately from the guide catheter 10 is inserted into the inside of the pusher catheter 20. Therefore, it is possible to separate the engagement between the stent 1 and the pusher catheter 20 by operating the stent releasing wire 90. As a result, if the guide catheter 10 has been retracted already, it is possible to replace the stent 1 at the accurate position.

By pulling the loop 91 through the stent releasing wire 90, the knot 81 of the stent connecting string 80 is unsnarled, and the engagement between the stent 1 and the pusher catheter 20 through the stent connecting string 80 is eliminated. Therefore, the releasing operation of the stent 1 can be easily performed.

Since the stent releasing wire 90 is made of resin, silk or metal, a frictional force between the stent releasing wire 40 and the pusher catheter 20 or between the stent releasing wire 40 and the guide catheter 10 is smaller than that of a stent releasing system by pulling the guide catheter such as the stent delivery system disclosed in the document of U.S. Pat. No. 5,921,952. Therefore, only slight pulling of the stent releasing wire 40 is required.

With this embodiment, each of the small holes is formed in the stent 1 by forming the notch 3 in the cylindrical wall of the stent 1, and the stent connecting string 80 is laced through the small hole 4. However, the stent connecting string 80 may be laced through the small hole 4a formed in the cylindrical wall of the stent 1 separately from the flap 2 (refer to FIG. 10). In addition, for example, the stent connecting string 80 may be hooked on the flap 2 of the stent 1 without the small hole 4 (refr to FIG. 11).

With this embodiment, similar to the first embodiment, the guide catheter 10 may be fixable to the pusher catheter 20 (refer to FIG. 12).

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A stent delivery system for delivering a stent,
   wherein the stent has a stent outer surface and a stent inner surface,
   wherein the stent inner surface defines a stent lumen, and
   wherein the stent has a proximal end face, the proximal end face of the stent defining a proximal opening of the stent lumen,
   wherein the stent delivery system comprises:
      a pusher catheter having a pusher catheter outer surface and a pusher catheter inner surface, the pusher catheter inner surface defining a pusher catheter lumen, wherein the pusher catheter has a distal end face, the distal end face of the pusher catheter defining a distal opening of the pusher catheter lumen;
      an elongated stent securing material having a fixed first portion fixed to the pusher catheter, a releasable second portion, and a releasable third portion, in that order, along a length of the elongated stent securing material,
         wherein in a secured configuration in which the stent and the pusher catheter are arranged in series along a longitudinal axis such that the proximal end face of the stent faces the distal end face of the pusher catheter, the releasable second portion is releasably connected to the stent and the releasable third portion is arranged in the pusher catheter lumen; and
      an elongated stent releasing material having a releasing portion configured to be retracted within the pusher catheter lumen along the longitudinal axis,
      wherein in the secured configuration of the stent and the pusher catheter, the releasing portion of the elongated stent releasing material is releasably connected to the releasable third portion of the elongated stent securing material to limit relative movement of the proximal end face of the stent and the distal end face of the pusher catheter along the longitudinal axis,
      wherein in the secured configuration of the stent and the pusher catheter, the releasable second portion, the fixed first portion, and the releasable third portion of the elongated stent securing material are disposed in that order along the longitudinal axis,
         wherein the releasable second portion is releasably connected to the stent at a more distal side than the fixed first portion along the longitudinal axis, and
         wherein the releasable third portion is releasably connected to the releasing portion of the elongated stent releasing material at a more proximal side than the fixed first portion along the longitudinal axis, and
      wherein in a released configuration of the stent and the pusher catheter, the releasing portion of the elongated stent releasing material is retracted within the pusher catheter lumen to be disconnected from the releasable third portion of the elongated stent securing material such that the releasable second portion of the elongated stent securing material is disconnected from the stent to permit relative movement of the proximal end face of the stent and the distal end face of the pusher catheter along the longitudinal axis.

2. The stent delivery system according to claim 1,
   wherein the stent defines a hole connecting the stent outer surface and the stent inner surface, and
   wherein the elongated stent securing material is configured such that in the secured configuration of the stent and the pusher catheter, the releasable second portion is laced through the hole of the stent to be releasably connected to the stent.

3. The stent delivery system according to claim 1,
   wherein the stent has a flap arranged on the stent outer surface, and
   wherein the elongated stent securing material is configured such that in the secured configuration of the stent and the pusher catheter, the releasable second portion is hooked to the flap of the stent to be releasably connected to the stent.

4. The stent delivery system according to claim 1,
wherein the releasable third portion of the elongated stent securing material is formed in a loop shape, and
wherein the releasing portion of the elongated stent releasing material has a higher rigidity than the releasable third portion of the elongated stent securing material.

5. The stent delivery system according to claim 1, wherein the elongated stent securing material has the fixed first portion, the releasable second portion, the releasable third portion, a releasable fourth portion, and a fixed fifth portion fixed to the pusher catheter, in that order, along the length of the elongated stent securing material, and wherein in the secured configuration, the releasable second portion and the releasable fourth portion are releasably connected to the stent and the releasable third portion is arranged in the pusher catheter lumen.

6. The stent delivery system according to claim 5,
wherein the pusher catheter defines:
a first hole connecting the pusher catheter outer surface and the pusher catheter inner surface, and
a second hole connecting the pusher catheter outer surface and the pusher catheter inner surface, and
wherein in the secured configuration, intermediate portions of the elongated stent securing material between the releasable second portion and the releasable third portion and the releasable fourth portion and the releasable third portion are arranged to extend through the first hole of the pusher catheter from the pusher catheter inner surface to the pusher catheter outer surface, and then extend through the second hole of the pusher catheter from the pusher catheter outer surface to the pusher catheter inner surface such that the releasable third portion is arranged in the pusher catheter lumen.

7. The stent delivery system according to claim 4, wherein the elongated stent releasing material is comprised of a wire made of resin or metal.

8. The stent delivery system according to claim 6,
wherein the first hole of the pusher catheter is formed between the distal end face of the pusher catheter and the second hole of the pusher catheter.

9. The stent delivery system according to claim 6,
wherein the first hole of the pusher catheter is separate from the second hole of the pusher catheter in a longitudinal direction of the pusher catheter from a distal end of the pusher catheter toward a proximal end of the pusher catheter, and
wherein the first and second holes of the pusher catheter are disposed to be closer to the proximal end of the pusher catheter than a bending area of the pusher catheter.

10. The stent delivery system according to claim 4, further comprising an operation portion, wherein the operation portion comprises an operation portion movable body operatively connected to the elongated stent releasing material and configured to be retracted by an operator to retract the elongated stent releasing material to disconnect the releasing portion of the elongated stent releasing material from the releasable third portion of the elongated stent securing material to switch the stent and pusher catheter from the secured configuration to the released configuration,
wherein the operation portion movable body has a movable scope which is longer than a length of a distal end of the elongated stent releasing material protruding from the loop shape.

11. The stent delivery system according to claim 10, wherein the operation portion further comprises stoppers configured to determine the movable scope of the operation portion movable body.

12. The stent delivery system according to claim 1, further comprising:
a guide catheter configured to be movably inserted and retracted along the longitudinal axis through the pusher catheter lumen and the stent lumen in the secured configuration of the stent and the pusher catheter.

13. The stent delivery system according to claim 12, wherein the guide catheter is configured such that:
in the secured configuration, the guide catheter is capable of being arranged in a space within the pusher catheter lumen adjacent to the releasing portion and the releasable third portion in a direction substantially orthogonal to the longitudinal axis, and
in the released configuration, the guide catheter is capable of being retracted along the longitudinal axis through the pusher catheter lumen to be clear of the space adjacent to the releasing portion and the releasable third portion.

14. The stent delivery system according to claim 12,
wherein the guide catheter defines a guide catheter lumen, and
wherein the stent delivery system further comprises:
a guide wire configured to be movably inserted and retracted within the guide catheter lumen.

* * * * *